United States Patent [19]

Medwid

[11] 4,341,212
[45] Jul. 27, 1982

[54] SEROUS FLUID DRAIN KIT

[76] Inventor: Albert Medwid, 770 Via Hierba, Santa Barbara, Calif. 93110

[21] Appl. No.: 170,146

[22] Filed: Jul. 18, 1980

[51] Int. Cl.³ .......................... A61M 1/00; A61M 5/00
[52] U.S. Cl. ................................ 128/276; 128/214.4
[58] Field of Search ................................ 128/276–278, 128/348, 760, 762, 763, 764, 766, 768, 770, 347, DIG. 26, DIG. 6, DIG. 9, 214.2, 214.4

[56] References Cited

U.S. PATENT DOCUMENTS

| | | | |
|---|---|---|---|
| 2,593,980 | 7/1950 | Calicchio | 128/350 |
| 2,712,822 | 7/1955 | Gewecke | 128/214.2 |
| 2,794,435 | 6/1957 | Stevens | 128/214.2 |
| 2,928,392 | 3/1960 | Burke | 128/214.2 |
| 3,233,610 | 2/1966 | Wade | 128/350 |
| 3,537,451 | 11/1970 | Murray et al. | 128/348 |
| 3,651,807 | 3/1972 | Huggins | 128/348 |
| 3,654,932 | 4/1972 | Newkirk et al. | 128/350 V |
| 3,680,562 | 8/1972 | Wittes | 128/349 R |
| 3,703,899 | 11/1972 | Calinog | 128/347 |
| 3,752,158 | 8/1973 | Kariher | 128/278 |
| 3,860,006 | 1/1975 | Patel | 128/347 |
| 3,874,367 | 4/1975 | Ayres | 128/350 V |
| 3,916,903 | 11/1975 | Pozzi | 128/347 |
| 3,982,546 | 9/1976 | Friend | 128/350 R |
| 4,192,304 | 3/1980 | Millet | 128/348 |
| 4,246,899 | 1/1981 | Loseff | 128/276 |

OTHER PUBLICATIONS

"Pin", Websters Dictionary, G. & C. Merriam Co., 1973.
"Apparatus for Rapid Collection of Blood Samples for Lactate and Pyruvate Determinations", Ewen et al., Lancet, Jan. 17, 1976, p. 127.

Primary Examiner—Kyle L. Howell
Assistant Examiner—J. L. Kruter
Attorney, Agent, or Firm—Fulwider, Patton, Rieber, Lee & Utecht

[57] ABSTRACT

A drain kit is provided for use in draining postoperative accumulations of serous fluid in patients without requiring immobilization of the patient or additional surgery. The kit comprises a catheter for insertion of a flexible cannula into the body region of serous fluid accumulation. The cannula is coupled to one end of a flexible drain tube carrying a piercing element at its opposite end for insertion through the self-sealing cap of a vacuum bottle for continuous drawing of the serous fluid from the patient. The piercing element is carried by a fitting having enlarged folding wings to facilitate insertion of the piercing element by the patient into the vacuum bottle and replacement bottles as needed, and attachment of the piercing element and the vacuum bottle to the patient's body or clothing.

19 Claims, 5 Drawing Figures

U.S. Patent     Jul. 27, 1982     4,341,212
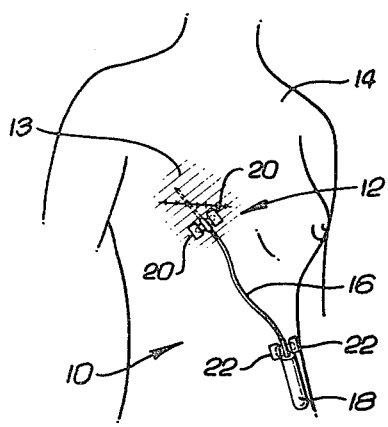
Fig. 1.
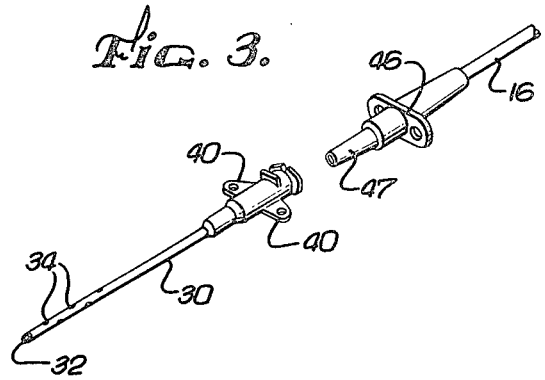
Fig. 3.
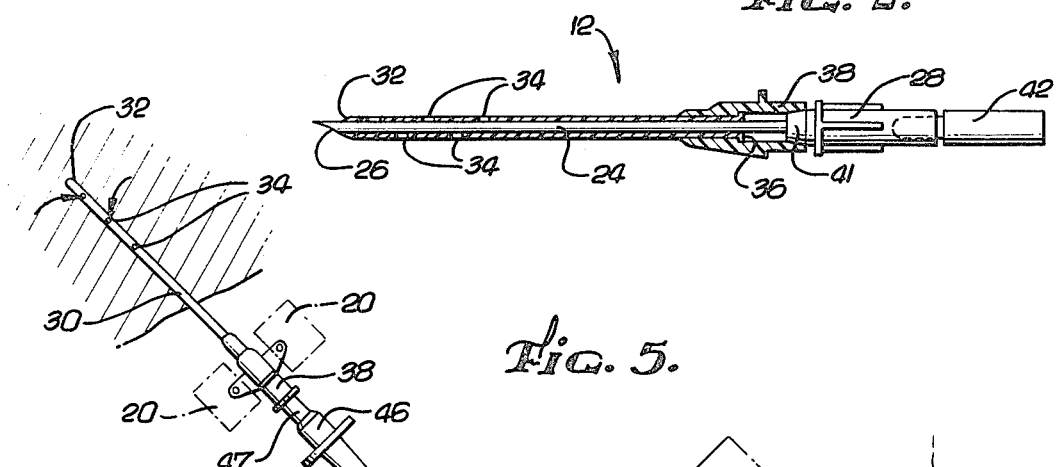
Fig. 2.
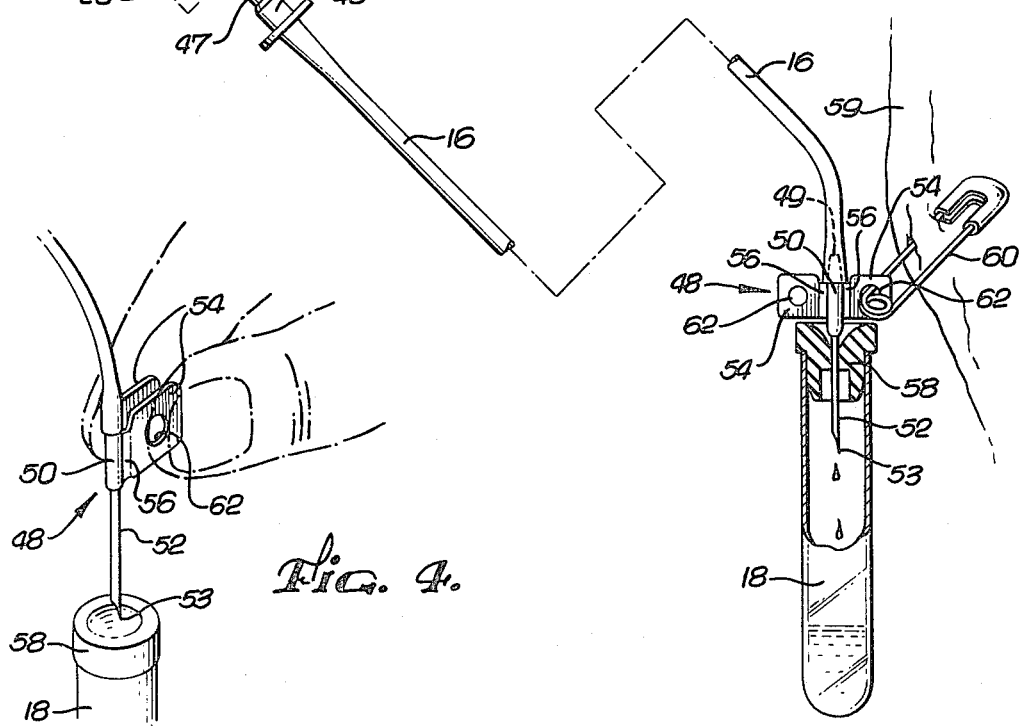
Fig. 5.
Fig. 4.

SEROUS FLUID DRAIN KIT

BACKGROUND OF THE INVENTION

This invention relates to a kit for use in draining fluids from the body of a patient. More specifically, this invention relates to a kit for continuously draining postoperative accumulations of serous fluid from a patient over relatively long periods of time without requiring immobilization of the patient or additional surgery.

Postoperative accumulations of serous fluid are frequently encountered in patients, particularly when the surgical procedure has required the loosening of relatively large flaps of skin from underlying subcutaneous tissue and deep fascia. For example, in the course of performing a radical mastectomy, the surgeon removes substantially all of the patient's breast tissue between the rib cage and a relatively large area of overlying skin. Following surgery, it is necessary for the resulting relatively large flap of skin to heal with and adhere to the underlying tissue. However, an accumulation of body fluid, typically referred to as serous fluid or a seroma, tends to collect between the overlying skin flap and the underlying tissue. This collection of serious fluid tends to prevent the skin from healing with the subcutaneous tissue and deep fascia, and also provides a medium highly susceptible to infection. It is therefore important that the accumulation of serous fluid be removed from the body as soon as possible to enable the tissues to heal properly and rapidly, and without infection. In the prior art, removal of such accumulations of serous fluid typically has been accomplished by means of additional surgery for purposes of re-exploration and additional suturing of the wound area.

A variety of devices and kits are available in the prior art for use in the collection or drainage of fluid from the body of a patient, and some of these devices have been proposed for draining accumulations of serous fluid. For example, a variety of surgically implanted drain tubes are available, but these tubes require additional surgery for implantation and further frequently require immobilization and/or hospitalization of the patient during the drainage period. See, for example, U.S. Pat. Nos. 2,593,980; 3,233,610; and 3,654,932. Other devices propose the insertion of a drainage tube by coupling of the tube to a suction source of the type typically available in hospitals. See, for example U.S. Pat. Nos. 3,680,562; 3,703,894 and 3,982,546. However, these devices also require immobilization of the patient in the hospital during the drainage period which can, in some instances, continue over a period of several days. One other proposal suggests a catheter-inserted drainage tube coupled to a periodically operated manual suction pump, but this arrangement is intended for periodic removal of fluid from the bladder and is thus not adapted for use in continuous drainage of accumulations of serous fluid. See U.S. Pat. No. 3,752,158. Finally, vacuum bottles carrying metal needles have been proposed for intravenous draining of small quantities of blood, but metal needles are ill-suited for retention in the patient's body over relatively long periods of time. See, for example, U.S. Pat. No. 3,874,367.

The present invention overcomes the problems and disadvantages of the prior art by providing an improved drain kit specifically adapted for the continuous collection of serous fluid from a patient to allow complete mobility and normal activity of the patient throughout the drainage period.

SUMMARY OF THE INVENTION

In accordance with the invention, a drain kit is provided for use in the collection and continuous drainage of body fluids such as accumulations of serous fluid which tend to accumulate in the vicinity of tissues separated during surgical procedures. The kit comprises a flexible cannula inserted nonsurgically directly into the region of accumulated serous fluid. The cannula is coupled via an adaptor fitting to a lightweight and portable source of vacuum in the form of a sterile vacuum bottle to enable the patient to carry on normal activity during the drainage period. The fitting is easily manipulated by the patient for removal and replacement of the vacuum bottle as needed.

The drain kit comprises a catheter assembly including an elongated trocar externally lined by a perforated cannula. The trocar and cannula are together inserted into the patient in the region of the serous fluid accumulation, whereupon the trocar is withdrawn to leave the cannula in place for collection and drainage of the serous fluid. An elongated flexible drain tube has a coupling at one end for connection to a mating coupling on the cannula. The opposite end of the drain tube carries the adaptor fitting including a piercing element for insertion into and through an elastomeric self-sealing cap of the sterile vacuum bottle. The fitting includes enlarged folding wings shaped for easy grasping by the patient to facilitate insertion of the piercing element into the vacuum bottle. The wings also provide structure by which the fitting and the vacuum bottle can be secured with respect to the patient as by taping to the patient's body, or by pinning to the patient's clothing. In use, the vacuum bottle provides a continuous vacuum source to draw the accumulated serous fluid continuously from the patient to promote postoperative healing without additional surgery or immobilization of the patient. The wings on the fitting facilitate quick and easy removal of a filled vacuum bottle by the patient, and insertion of the piercing element into a new vacuum bottle.

Other features and advantages of the present invention will become apparent from the following detailed description, taken in conjunction with the accompanying drawings which illustrate by way of example the principles of the invention.

BRIEF DESCRIPTION OF THE DRAWINGS

The accompanying drawings illustrate the invention. In such drawings:

FIG. 1 is a perspective view illustrating use of the drain kit of this invention;

FIG. 2 is an enlarged elevation view, partially in section, showing a catheter assembly for use in the kit of this invention;

FIG. 3 is a perspective view illustrating by way of example an intermediate step in the use of the kit of this invention;

FIG. 4 is an enlarged fragmented perspective view illustrating a subsequent step in the use of the kit of this invention; and FIG. 5 is an enlarged elevation view illustrating use of the drainage kit in detail, with portions broken away.

DETAILED DESCRIPTION OF THE PREFERRED EMBODIMENT

The drain kit 10 of this invention is illustrated in use in FIG. 1. The kit 10 generally comprises a catheter assembly 12 for insertion into the body of a patient 14 in a region 13 requiring drainage of a body fluid such as an accumulation of serous fluid. The catheter assembly is coupled to a flexible drainage tube 16 which in turn connects to a relatively compact and lightweight source of vacuum in the form of a sterile vacuum bottle 18. The entire kit 10 can be attached directly to the patient 14, as by strips of tape 20 and 22 illustrated in FIG. 1 to allow complete mobility and normal activity of the patient 14 throughout the drainage period.

The drain kit 10 comprises a plurality of sterile components which may be safely installed and used in the collection of the serous fluid without fear of risking infection and without requiring additional surgery or immobilization of the patient. The kit is adapted for non-surgical installation such as, for example, in the office of a physician, whereupon the patient can be allowed immediately to return home to resume normal activity without substantial discomfort. The accumulation of serous fluid is drawn continuously over from the patient's body by means of the vacuum bottle 18, and when filled, the vacuum bottle can be removed and replaced with a new one by the patient without fear or risk of infection, and without requiring a return to a medical facility. Accordingly, the drain kit of this invention provides for safe and effective drainage of the serous fluid accumulation over an extended period of time with minimum patient discomfort and inconvenience.

As illustrated in FIG. 2, the catheter comprises an elongated hollow metal trocar 24 having a sharp beveled tip 26 at its forward end. The rear end 28 of the trocar is carried by a hollow housing 28 which is conveniently closed by a plug 42. A sheath-like cannula 30 is formed from a suitable lightweight and flexible surgical material such as polyethylene and is snugly and slidably received over the trocar 24. The cannula 30 has a relatively blunt forward end 32 terminating near the tip 26 of the trocar 24, and a plurality of perforations 34 near its forward end 32 for admission of body fluid to the interior of the cannula 30, as will be described in more detail. The rear end of the cannula 30 includes an enlarged flange 36 fixed within a rearwardly open female coupling 38 including a pair of outwardly projecting wings 40 (FIG. 3). Conveniently, as shown in FIG. 2, the hollow trocar housing 28 includes a forwardly projecting plug 41 for reception into and closing of the female coupling 38 to maintain sterility of the assembly 12 prior to use.

The trocar 24 of the catheter assembly 12 is inserted directly into the region of the patient's body wherein serous fluid has or is expected to collect. For example, as illustrated in FIG. 1, the trocar 24 is inserted directly into a body region 13 underlying the relatively large flap of skin which remains following a surgical procedure such as a radical mastectomy. In such a surgical procedure, the resultant large flap of skin is required to heal with a relatively large area of subcutaneous tissue and deep fascia overlying the rib cage following surgical removal of the patient's breast tissue. Following this type of surgical procedure, the accumulation of serous fluid, commonly referred to as a seroma, is frequently encountered in the region between the overlying skin flap and the underlying tissue, and this serous fluid must be removed promptly to promote proper healing. Therefore, to collect and remove this serous fluid, the trocar 24 is inserted directly into the region 13, typically in a position slightly below the surgical suture line 44.

Insertion of the trocar 24 into the body region 13 of serous fluid accumulation serves also to insert the flexible cannula 30 into the body region 13. As this time, the trocar 26 is withdrawn from the cannula 30 by manually grasping and pulling upon the trocar housing 28 while maintaining the cannula 30 and its accompanying female coupling 38 in a secure position with the cannula 30 projecting into the region 13. Immediately upon withdrawal of the trocar, the flexible drain tube 16 is coupled directly to the female coupling 38 as viewed in FIG. 3 by means of a complementary-shaped male member 47 projecting outwardly from a coupling 46 at one end of the drain tube 16. This drain tube 16 is conveniently formed from a length of sterile, flexible material such as polyethylene or the like.

The opposite end of the drain tube 16 receives a projecting member 49 of a fitting 48 comprising a sterilized plastic sleeve 50, as shown in FIGS. 4 and 5. This sleeve 50 carries a piercing element 52 in the form of a relatively short hollow needle having a sharp beveled tip 53. The fitting 48 further includes a pair of oppositely-disposed, outwardly projecting wings 54 which are foldable with respect to the fitting sleeve 50 along score lines 56. These wings 54 are easily grasped as illustrated in FIG. 4 for manually carrying and inserting the piercing element 52 into and through an elastomeric self-sealing cap 58 closing the upper end of the sterile vacuum bottle 18. In this configuration, the accumulated serous fluid from the region 13 of the patient's body 14 is drawn continuously over a period of time by the vacuum in the vacuum bottle 18 through the cannula 30 and the drain tube 16 into the vacuum bottle 18 for collection over an extended period of time.

As illustrated in FIG. 1, the drain kit 10 is quickly and easily secured directly to the patient 14 as by means of the tape strips 20 overlying the wings 40 of the cannula female coupling 38. Similarly, the tape strips 22 can be provided overlying the wings 54 of the drain tube fitting 48. If desired, additional tape strips (not shown) can be provided for affixing the vacuum bottle 18 directly to the patient's body. Alternately, as illustrated in FIG. 5, the vacuum bottle 18 and the drain tube fitting 48 can be conveniently secured directly to the patient's clothing 59 as by means of a safety pin 60 or the like received through holes 62 formed in the wings 54.

The vacuum bottle 18 is relatively compact and lightweight, and can be carried about attached directly to the patient or to the patient's clothing. The drain kit 10 thus does not restrict the mobility or the activity of the patient, but instead allows the patient to carry on normal activity throughout an extended period of time while the serous fluid is being drained. When the vacuum bottle 18 fills with collected serious fluid, the bottle 18 is quickly and easily removed by the patient 14 without the assistance of a physician or other medical personnel by manually grasping the wings 54 on the drain tube fitting 48 to withdraw the piercing element 52 from the filled bottle. Following this, the filled bottle 18 can be discarded, and the piercing element 52 inserted through the self-sealing cap 58 of an unfilled replacement vacuum bottle. Importantly, the foldable wings 54 on the fitting 48 not only serve to provide means for attaching the kit to the patient, but also provide structure which is easily grasped and manipulated by the patient without assistance to facilitate accurate location and handling of the piercing element 52 during replacement of the vacuum bottle. This structure is particularly advantageous when the drain kit 10 is used for collection and drainage of serous fluid following a radical mastectomy since the patient typically has difficulty seeing and handling the piercing element 52 and the vacuum bottle 18 in the vicinity of the patient's waistline.

A variety of modifications and improvements to the drain kit of this invention are believed to be apparent to one skilled in the art. Accordingly, no limitation on the invention is intended, except as set forth in the appended claims.

I claim:

1. A drain kit for collection and drainage of serous fluid from a prescribed region of accumulated serous fluid in a patient's body comprising:
   a catheter assembly including a flexible cannula having a plurality of perforations formed therein and slidably carried by an elongated trocar, said trocar being insertable into said prescribed body region to insert one end of said cannula into said region, and slidably removable from said cannula to leave said cannula inserted into said region for collection of the fluid and for passage thereof through the cannula out of the patient's body;
   an elongated drain tube having one end for connection to said cannula for receiving the fluid drained through said cannula;
   a portable vacuum bottle defining a source of continuous vacuum and including a self-sealing cap of a resilient material;
   a fitting at the other end of said drain tube and including a hollow piercing element for insertion through said cap for draining of the fluid from said tube into said bottle, said fitting further including at least one outwardly projecting wing sized to facilitate manual grasping of said fitting for easy insertion of said piercing element through said cap, and subsequent removal from said cap when the bottle is filled with the draining fluid; and
   means cooperating with said wing adapted for securing said fitting with respect to the patient's body.

2. The drain kit of claim 1 wherein said fitting comprises a central sleeve carrying said piercing element, and wherein said at least one wing comprises a pair of wings projecting outwardly from said sleeve.

3. The drain kit of claim 2 wherein said fitting is formed from a plastic material, and wherein said wings are foldable with respect to said sleeve along respective score lines between said sleeve and said wings.

4. The drain kit of claim 1 wherein said piercing element comprises a hollow needle.

5. The drain kit of claim 1 wherein said securing means comprises a strip of tape adapted for attaching said fitting to the patient's body.

6. The drain kit of claim 1 wherein said securing means comprises a pin adapted for attaching said fitting to clothing worn by the patient.

7. The drain kit of claim 6 wherein said wing includes a hole formed therein for reception of said pin.

8. The drain kit of claim 1 including a plurality of said vacuum bottles for removable reception one at a time of said piercing element for drawing the fluid from said prescribed body region.

9. The drain kit of claim 1 including complementary-shaped couplings connected respectively to the end of said cannula outside the patient's body and to said one end of said drain tube, said complementary-shaped couplings being for securing together subsequent to removal of said trocar from said cannula.

10. The drain kit of claim 1 wherein said cannula comprises a hollow flexible tubular sheath having a blunt end for reception into said prescribed body region, said plurality of perforations being formed generally adjacent said blunt end.

11. A drain kit for collection and drainage of serous fluid from a region of accumulated serous fluid in a patient's body; comprising:
    a catheter assembly including a hollow flexible cannula having a blunt end with a plurality of perforations formed adjacent said blunt end and a rear end connected to a female coupling member, and a relatively rigid trocar with a pointed end and received slidably within said cannula and said female coupling member, said pointed end of said trocar being insertable into said region of accumulated serous fluid to carry said blunt end of said cannula into said region, said trocar being slidably removable from said cannula and said female coupling member to leave said blunt end of said cannula within said region for collection and passage of the serous fluid out of the patient's body;
    an elongated flexible drain tube having a male coupling member carried at one end for reception into said female coupling member for communicating the interior of said drain tube with the interior of said cannula;
    a portable vacuum bottle defining a source of continuous vacuum and including a self-sealing resilient cap;
    a fitting at the other end of said drain tube and including a hollow piercing element for insertion through said cap for coupling said vacuum to the interior of said tube whereby said vacuum draws the serous fluid from the patient's body into said bottle, said fitting further including a pair of foldable wings projecting outwardly and sized to facilitate manual grasping of said fitting for easy insertion of said piercing element through said cap, and subsequent removal from said cap when the bottle is filled with the draining fluid;
    and
    means cooperating with said wings adapted for securing said fitting with respect to the patient's body.

12. The drain kit of claim 11 wherein said securing means comprises a pin adapted for attaching said fitting to clothing worn by the patient, at least one of said wings having a hole formed therein for reception of said pin.

13. A drain kit for collection and drainage of serous fluid from a region of accumulated serous fluid in a patient's body, comprising:
    a catheter assembly including a hollow flexible cannula having a blunt end with a plurality of perforations formed adjacent said blunt end and a rear end connected to a female coupling member, and a relatively rigid trocar having a pointed end and received slidably within said cannula and said female coupling member, said pointed end of said trocar being insertable into said region of accumulated serous fluid to carry said blunt end of said cannula into said region, said trocar being slidably removable from said cannula and said female coupling member to leave said blunt end of said cannula within said region for collection and passage of the serious fluid out of the patient's body;

an elongated flexible drain tube having a male coupling member carried at one end for reception into said female coupling member for communicating the interior of said drain tube with the interior of said cannula;

a plurality of portable vacuum bottles each defining a source of continuous vacuum and including a self-sealing resilient cap;

a fitting at the other end of said drain tube and including a hollow piercing element for insertion through the cap of one of said bottles for coupling the vacuum therein to the interior of said tube whereby the vacuum draws the serous fluid from the patient's body into said one bottle, said bottles being for successive reception of said piercing element and successive filling with the serous fluid, said fitting further including a pair of foldable wings projecting outwardly and sized to facilitate manual grasping of said fitting for easy insertion of said piercing element through said cap, and subsequent removal from said cap when the bottle is filled with the draining fluid; and means cooperating with said wings for securing said fitting with respect to the patient's body.

14. A method of collecting and draining fluid from a prescribed region of a patient's body, comprising the steps of:

inserting one end of a flexible cannula having a plurality of perforations formed therein into the prescribed body region by inserting a trocar slidably carrying the cannula into said region and slidably removing the trocar from the cannula to leave the cannula inserted into said region for collection and passage of the fluid out of the patient's body;

coupling one end of an elongated drain tube to the cannula for reception of the fluid drained through the cannula;

providing a fitting with at least one outwardly projecting wing at the opposite end of the drain tube including a hollow piercing element for passage of the fluid from the tube;

passing the piercing element through a self-sealing resilient cap of a portable vacuum bottle to couple the body region to the vacuum within the bottle to draw the fluid continuously into the bottle for an extended period of time; and securing the fitting with respect to the patient's body with securing means cooperating with said wing.

15. The method of claim 14 including the steps of providing a plurality of the portable vacuum bottles each with a self-sealing resilient cap, and passing the piercing element through the cap of successive ones of said bottles to fill said bottles in succession with the serous fluid.

16. A drain kit for collection and drainage of fluid from a prescribed region of a patient's body comprising:

a catheter assembly including a flexible cannula slidably carried by an elongated trocar, said trocar being insertable into said prescribed body region to insert one end of said cannula into said region, and slidably removable from said cannula to leave said cannula inserted into said region for collection of the fluid and for passage thereof through the cannula out of the patient's body;

an elongated drain tube having one end for connection to said cannula for receiving the fluid drained through said cannula;

a portable vacuum bottle defining a source of vacuum and including a self-sealing cap of a resilient material;

and a fitting at the other end of said drain tube and including a hollow piercing element for insertion through said cap for draining of the fluid from said tube into said bottle, said fitting further including at least one outwardly projecting wing sized to facilitate manual grasping of said fitting for easy insertion of said piercing element through said cap and subsequent removal from said cap when the bottle is filled with the draining fluid, and securing means cooperating with said wing adapted for connection to clothing worn by the patient to secure said fitting with respect to the patient's body.

17. The drain kit of claim 16 wherein said securing means comprises a pin.

18. A drain kit of claim 17 wherein said wing has a hole formed therein for reception of said pin.

19. A drain kit for collection and drainage of serous fluid from a region of accumulated serous fluid in a patient's body, comprising:

a catheter assembly including a hollow flexible cannula having a blunt end with a plurality of perforations formed adjacent said blunt end and a rear end connected to a female coupling member, and a relatively rigid trocar with a pointed end and received slidably within said cannula and said female coupling member, said pointed end of said trocar being insertable into said region of accumulated serous fluid to carry said blunt end of said cannula into said region, said trocar being slidably removable from said cannula and said female coupling member to leave said blunt end of said cannula within said region for collection and passage of the serous fluid out of the patient's body;

an elongated flexible drain tube having a male coupling member carried at one end for reception into said female coupling member for communicating the interior of said drain tube with the interior of said cannula;

a portable vacuum bottle defining a source of vacuum and including a self-sealing resilient cap;

a fitting at the other end of said drain tube and including a hollow piercing element for insertion through said cap for coupling said vacuum to the interior of said tube whereby said vacuum draws the serous fluid from the patient's body into said bottle, said fitting further including at least one foldable wing projecting outwardly and sized to facilitate manual grasping of said fitting for easy insertion of said piercing element through said cap and subsequent removal from said cap when the bottle is filled with the draining fluid, said at least one wing having a hole formed therein; and a pin receivable through the hole formed in said at least one wing and adapted for connection to clothing worn by the patient to secure said fitting with respect to the patient's body.

* * * * *